US007463359B2

(12) United States Patent
Hyde

(10) Patent No.: US 7,463,359 B2
(45) Date of Patent: Dec. 9, 2008

(54) PLASMON TOMOGRAPHY

(75) Inventor: Roderick A. Hyde, Livermore, CA (US)

(73) Assignee: Searete LLC

(*) Notice: Subject to any disclaimer, the term of this patent is extended or adjusted under 35 U.S.C. 154(b) by 210 days.

(21) Appl. No.: 11/402,305

(22) Filed: Apr. 11, 2006

(65) Prior Publication Data

US 2007/0190639 A1 Aug. 16, 2007

Related U.S. Application Data

(63) Continuation-in-part of application No. 11/355,918, filed on Feb. 16, 2006.

(51) Int. Cl.
*G01N 21/00* (2006.01)

(52) U.S. Cl. ........................................ 356/445

(58) Field of Classification Search .................... None
See application file for complete search history.

(56) References Cited

U.S. PATENT DOCUMENTS

| | | | | |
|---|---|---|---|---|
| 4,063,549 | A | 12/1977 | Beretsky et al. | |
| 4,646,256 | A | 2/1987 | Bracewell | |
| 5,025,147 | A * | 6/1991 | Durig et al. | 250/216 |
| 6,980,716 | B1 | 12/2005 | Diaz et al. | |
| 2002/0044285 | A1 | 4/2002 | Pedersen et al. | |
| 2003/0127429 | A1 | 7/2003 | Ohgaki | |
| 2004/0141702 | A1 | 7/2004 | Fuflyigin et al. | |
| 2004/0218185 | A1 | 11/2004 | Yamada et al. | |
| 2004/0228577 | A1 | 11/2004 | Pezeshki et al. | |
| 2005/0191427 | A1 | 9/2005 | Wade et al. | |
| 2005/0281996 | A1 | 12/2005 | Harbron et al. | |
| 2006/0014084 | A1 | 1/2006 | French et al. | |

OTHER PUBLICATIONS

Barnes, William L.; Dereux, Alain; Ebbesen, Thomas W.; "Surface Plasmon Subwavelength Optics"; Nature; Aug. 14, 2003; pp. 824-830; vol. 424; Nature Publishing Group.

Lopez, R; Boatner, L.A.; Haynes, T.E.; Feldman, L.C.; and Haglund Jr., R.F.; "Synthesis and Characterization of Size-Controlled Vanadium Dioxide Nanocrystals in a Fused Silica Matrix"; Journal of Applied Physics; Oct. 1, 2002; also bearing dates of Feb. 6, 2002, Jul. 3, 2002, and Sep. 18, 2002; pp. 4031-4036; vol. 92, Issue No. 7; American Institute of Physics.

* cited by examiner

*Primary Examiner*—Michael P Stafira

(57) ABSTRACT

Plasmon energy is produced by exciting a plasmon resonance at least one excitation position on a first surface of a first material, and the plasmon energy is detected at at least one measurement position on the first surface after the plasmon energy has propagated from the at least one excitation position to the at least one measurement position. An attenuation of plasmon energy is determined along a plurality of paths between the at least one excitation position and the at least one measurement position, and relative distances between the first surface and a second surface of a second material are determined at a plurality of points on at least one of the surfaces based on the determined attenuation of plasmon energy along the plurality of paths.

17 Claims, 11 Drawing Sheets

PLASMON TOMOGRAPHY

RELATED APPLICATIONS

For purposes of the USPTO extra-statutory requirements, the present application constitutes a continuation-in-part of U.S. patent application Ser. No. 11/355,918, entitled PLASMON TOMOGRAPHY, naming Roderick A. Hyde as inventor, filed 16 Feb. 2006, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette March 18, 2003, available at http://www.uspto.gov/web/offices/com/sol/og/2003/week11/patbene.htm. The present applicant entity has provided above a specific reference to the application(s)from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates, in general, to plasmon tomography.

BACKGROUND

Surface plasmon resonances ("plasmons") can be excited at the interface of materials having different dielectric properties. Plasmons are described generally in C. Kittel, "Introduction to Solid State Physics," Wiley, 1995, which is incorporated herein by reference.

SUMMARY

According to one general aspect, a method includes producing plasmon energy by exciting a plasmon resonance at least one excitation position on a first surface of a first material and detecting the plasmon energy at least one measurement position on the first surface after the plasmon energy has propagated from the at least one excitation position to the at least one measurement position. An attenuation of plasmon energy is determined along a plurality of paths between the at least one excitation position and the at least one measurement position, and relative distances between the first surface and a second surface of a second material are determined at a plurality of points on at least one of the surfaces based on the determined attenuation of plasmon energy along the plurality of paths.

Implementations may include one or more of the following features. For example, the method can further include determining absolute distances between the first surface and the second surface at the plurality of points based on the relative distances and on a known distance between the first surface and the second surface at one of the points. The first surface can include a conductive layer. The first surface can define a part of a material that includes a photonic crystal.

The method can further include detecting plasmon energy at a plurality of measurement positions along a periphery of the first surface. The method can further include exciting plasmon resonances at a plurality of excitation positions along a periphery of the first surface and/or detecting plasmon energy at a plurality of measurement positions along a periphery of the first surface.

Exciting a plasmon resonance can include providing optical energy to the first surface, and providing optical energy to the first surface can include illuminating at least a portion of the first surface with laser light. Exciting a plasmon resonance can also include providing a coherent beam of electromagnetic radiation to the first surface.

At least one of the first or second surfaces can define a portion of a mask and the other of the first or second surfaces can define a portion of a substrate. The mask can include a plurality of plasmon guides on the first surface, and the plasmon guides can define the plurality of paths on the first surface. The plurality of plasmon guides can be disposed substantially parallel to one another on the first surface. The method can further include exciting plasmon resonances at excitation positions substantially located at first ends of each of the plurality of plasmon guides and detecting plasmon energy at measurement positions substantially located at second ends of each of the plurality of plasmon guides.

The method can further include providing the first material having the first surface and providing the second material having the second surface facing the first surface. The first surface can be a patterned surface, and the second material can include a polymer, and the method can further include heating the second material above a polymer-glass transition temperature until a pattern corresponding to the patterned surface of the first surface is created in the second material and cooling the second material below the polymer-glass transition temperature.

The method can further include altering the first or second surface after determining relative distances between the first surface and the second surface. For example, plasmon energy can be produced by exciting a plasmon resonance at least one excitation position on the first surface after altering the first or second surface, and then, after altering the first or second surface, the plasmon energy can be detected at least one measurement position on the first surface after the plasmon energy has propagated from the at least one excitation position to the at least one measurement position. After altering the first or second surface, an attenuation of plasmon energy along a plurality of paths between the at least one excitation position and the at least one measurement position can be determined and relative distances between the first surface and the second surface can be determined at a plurality of points on at least one of the surfaces after altering the first or second surface based on the determined attenuation of plasmon energy along the plurality of paths. Altering the first or second surface can include moving a micro-electro-mechanical structure on the altered surface, moving a structure across the altered surface, or catalyzing a reaction between materials of the first or second surface and another material.

In another general aspect, a method includes producing plasmon energy by exciting a plasmon resonance at least one excitation position on a first surface of a first material facing a second surface of a second material and detecting an amount of plasmon energy at a measurement position on the first surface after the plasmon energy has propagated from the excitation position to the measurement position. A relative position between the first and second surfaces is adjusted based on the amount of plasmon energy detected at the measurement position.

Implementations may include one or more of the following features. For example, the second material can include a semiconductor material and the first material can include a patterned mask. The method can further include providing the first material having the first surface and providing the second material having the second surface facing the first surface. The method can include producing plasmon energy by exciting a plasmon resonance at the at least one excitation position on the first surface, detecting an amount of plasmon energy at the measurement position on the first surface after the plasmon energy has propagated from the excitation position to the measurement position, and adjusting a relative position between the first and second surfaces based on the amount of plasmon energy detected at the measurement position until the amount of plasmon energy detected at the measurement position is substantially equal to a desired amount of plasmon energy.

The first surface can include a first deformity, and the second surface can include a second deformity. For example, the first deformity and the second deformity can be protrusions from the surfaces. The first and second deformities can be aligned along a direction substantially perpendicular to the first and second surfaces when the measured amount of plasmon energy is substantially equal to the desired amount of plasmon energy.

According to another general aspect, an apparatus includes positioning structures configured to align a first surface of a first material with a second surface of a second material, an optical energy source, a detector, and a processor. The source is alignable to provide electromagnetic radiation at a frequency responsive to excite a plasmon resonance at at least one excitation position on a first surface of the first material. The detector is configured to produce a signal corresponding to excited plasmon energy at least one measurement position on the first surface spatially separated from the at least one excitation position. The processor is responsive to the signal corresponding to excited plasmon energy at least one measurement position and configured to determine at least one separation distance between the first material and the second material.

Implementations may include one or more of the following features. For example, the processor can be further configured to determine an attenuation of plasmon energy along a path between the at least one excitation position and the at least one measurement position and can be configured to determine at least one separation distance between the first surface and the second surface based at least in part on the determined attenuation of plasmon energy along the path. The processor can also be configured to determine an attenuation of plasmon energy along a plurality of paths between the at least one excitation position and the at least one measurement position and an be configured to determine at least one separation distance between the first surface and the second surface based at least in part on the determined attenuation of plasmon energy along the plurality of paths.

The optical source can be a laser. The first surface can include a conductive layer and/or can define a part of a material comprising a photonic crystal. The optical energy source can be configured to excite plasmon resonances at a plurality of excitation positions along a periphery of the first surface. The detector can be further configured to produce signals corresponding to excited plasmon energy at a plurality of measurement positions along a periphery of the first surface spatially separated from the at least one excitation position. At least one of the first or second surfaces can define a portion of a mask, and the other of the first or second surfaces can define a portion of a substrate. The mask can include a plurality of plasmon guides on the first surface and the plasmon guides can define the plurality of paths on the first surface. The plurality of plasmon guides can be disposed substantially parallel to one another on the first surface. The optical energy source can be further configured to excite plasmon resonances at excitation positions substantially located at first ends of each of the plurality of plasmon guides; and the detector can be configured to produce signals corresponding to excited plasmon energy at measurement positions substantially located at second ends of each of the plurality of plasmon guides.

The first surface can be a patterned surface, and the second material can include a polymer, and the apparatus can also include a heat source configured to heat the second material above a polymer-glass transition temperature until a pattern corresponding to the patterned surface of the first surface is created in the second material. The detector can include a coupler, which can include, e.g., a diffraction grating, adapted for coupling plasmon energy at the measurement position into an electromagnetic wave.

In another general aspect, an apparatus includes positioning structures configured to align a first surface of a first material with a second surface of a second material, an optical energy source, and a detector. The source is alignable to provide electromagnetic radiation at a frequency responsive to excite a plasmon resonance at least one excitation position on a first surface of the first material. The detector is configured to produce a signal corresponding to excited plasmon energy at least one measurement position on the first surface spatially separated from the at least one excitation position. And the positioning structures are configured to adjust a relative position between the first and second surfaces in response to the signal.

Implementations may include one or more of the following features. For example, the positioning structures can include a movable stage configured to align the first surface with the second surface, and the apparatus can further include a processor configured to process the signal corresponding to excited plasmon energy to provide a signal to the movable stage to move the first or second surfaces into an alignment position with the other of the first or second surface.

The second material can include a semiconductor material and/or the first material can include a patterned mask. The first surface can include a first deformity and the second surface can include a second deformity. The first deformity and the second deformity can be protrusions from the surfaces. The detector can be configured to produce a signal corresponding to an amount of excited plasmon energy at the at least one measurement position on the first surface, and the positioning structures can be configured to align the first deformity and the second deformity along a direction substantially perpendicular to the first with second surfaces when the detected amount of plasmon energy is substantially equal to a desired amount of plasmon energy.

The detector can include a coupler adapted for coupling plasmon energy at the measurement position into an electromagnetic wave. The coupler can include a diffraction grating.

In another general aspect, an article includes a machine-accessible medium that stores executable instructions that cause electrical circuitry to acquire data about an attenuation of plasmon energy along a plurality of paths between the at least one plasmon excitation position on a first surface of a first material facing a second surface of a second material and the at least one measurement position on the first surface and determine relative distances between the first surface and a second surface of a second material at a plurality of points on at least one of the surfaces based on the determined attenuation of plasmon energy along the plurality of paths.

Implementations may include one or more of the following features. For example, the instructions can further cause the electrical circuitry to acquire data about a known distance between the first surface and the second surface at least one point on the first surface and to determine absolute distances between the first surface and the second surface at the plurality of points based on the relative distances and on the at least one point on the first surface. The instructions can further cause the electrical circuitry to generate a control signal to which positioning structures respond by moving the first or second surface relative to the other surface.

In another general aspect, an article includes a machine-accessible medium that stores executable instructions that cause electrical circuitry to acquire data about an amount of plasmon energy at a measurement position on a first surface facing a second surface separated from a measurement position from which the plasmon energy has propagated, to compare the amount of plasmon energy to a predetermined amount, and to generate a control signal to which positioning structures respond by moving the first or second surface relative to the other surface.

The details of one or more implementations are set forth in the accompanying drawings and the description below. Other features will be apparent from the description and drawings, and from the claims.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
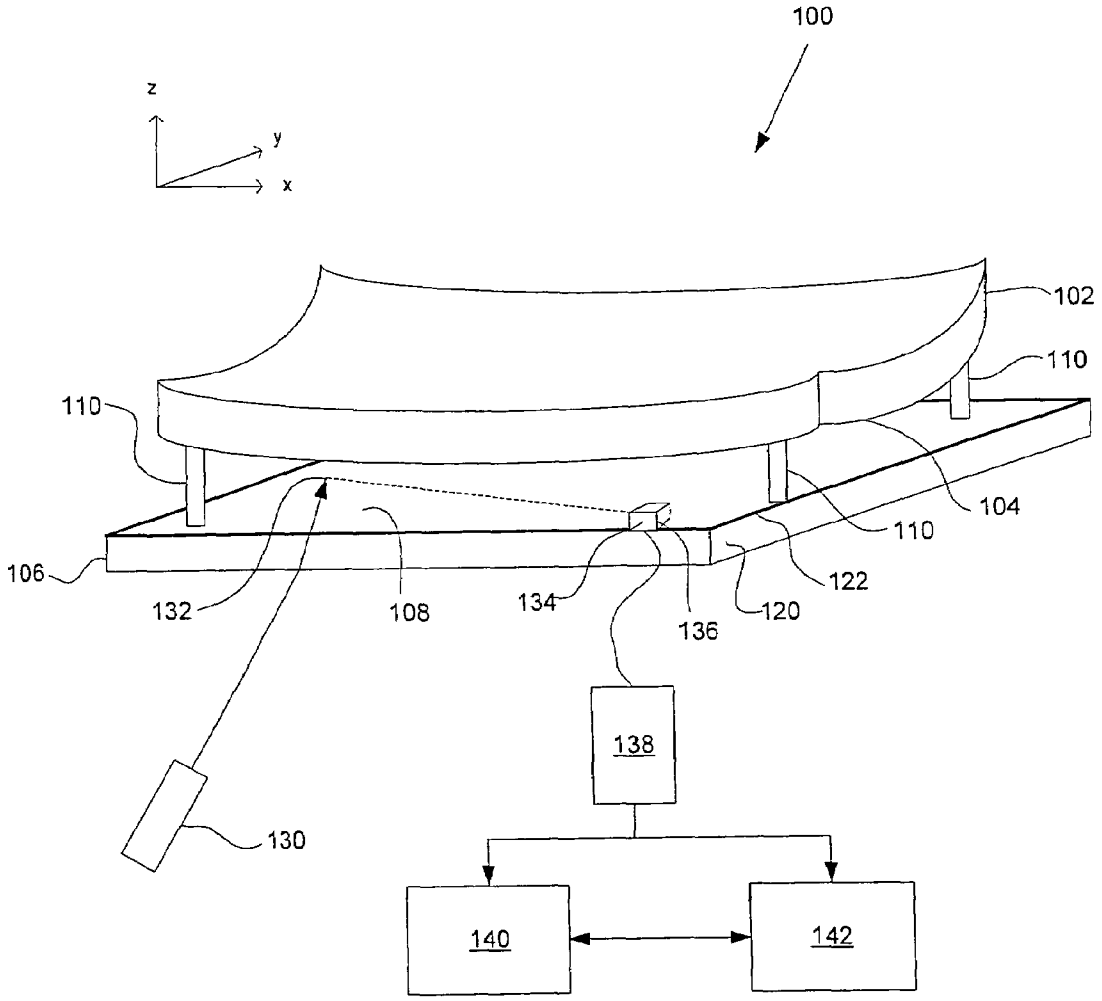
FIG. 1 is schematic perspective view of a system for creating an image of a surface using surface plasmon tomography.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

One or more implementations are described below. It should be noted that these implementations are exemplary and are intended to be illustrative rather than limiting. It is impossible to include all of possible implementations and contexts of the invention in this disclosure.

FIG. 1 is a schematic perspective view of a system 100 for determining distances between two surfaces and for creating an image of a surface using surface plasmon tomography. An object 102 having a surface 104 to be imaged is placed in close proximity to the surface 108 of another object 106. Positioning structures 110 position the objects 102 and 106 relative to each other, such that the surfaces 104 and 108 are in close proximity to each other. The positioning structures can be static spacers. For example, the positioning structures 110 can be structures having a predetermined height that are deposited or epitaxially grown on one of the surfaces 104 or 108 or, when one or both surfaces 104 or 110 are rough the dedicated spacers can be omitted and the positioning structures 110 can be portions of the surfaces that rise above other portions of the surfaces and contact the opposite surface. The positioning structures 110 can also be moveable structures that can adjust dynamically the distance between surfaces 104 and 110. For example, the positioning structures 110 can be piezoelectric pillars that can change independently the distance between surfaces 104 and 108 at different positions on the surfaces. The positioning structures 110 also can be part of an x-y-z stage that can move either object 102 or object 106, such that surfaces 104 and 108 are moved relative to each other, either parallel or perpendicular to the surfaces.

The object 106 can include two layers 120 and 122 having different dielectric constants, so that a surface plasmon resonance can be excited at the interface between the two layers. To support a surface plasmon resonance, the real parts of the dielectric constants of the two layers have opposite signs at a particular excitation frequency. For example, the layer 120 can be an insulator or a semiconductor layer with a dielectric constant having a positive real part, and the layer 122 can be a thin conductive film (e.g., a gold or silver film) with a dielectric constant having a negative real part.

A source of optical energy 130 can direct optical energy to the interface between layers 120 and 122 to excite a surface plasmon resonance at an excitation position 132 on the surface 108 of the object 106. The source 130 can be a source of coherent electromagnetic energy, e.g., a laser that generates electromagnetic waves having a frequency that resonates with the surface plasmon resonance. The optical energy can be directed from the bottom of the layer 120 through layer 120 to the interface between layers 120 and 122 when the layer is transparent to the optical energy. Alternatively, the source 120 can be positioned above the object 106 and shined directly onto the surface 108, with the beam path of the optical energy passing either between objects 106 and 102 or through object 102. The beam path of the optical energy also can pass through the object 102 when the object 102 is transparent to the optical energy. In still another implementation, the light source 130 can be located on or within the object 106 and can energized to shine optical energy toward the interface between layers 120 and 122. For example, the source 130 can include one or more light emitting diodes (LEDs) or semiconductor lasers fabricated within layers of the object 106, and the light output from the LEDs or semiconductor lasers can be directed to the interface of the layers 120 and 122 to excite a surface plasmon resonance.

When the surface plasmon resonance is excited at the excitation position 132, energy in the resonance can travel on the surface 108 to a detection position 134 at which an amount of energy in the resonance can be detected. For example, a coupler 136 at the detection position can couple energy in the surface plasmon resonance into optical energy that can be transported in a waveguide (e.g., an optical fiber) to an optical energy detector 138 that detects an optical signal proportional the plasmon energy at the detection position 134. The output of the detector 138 can be fed into a processor 140 and/or stored in a memory 142 and used to determine distances between surfaces 104 and 104 and/or to create an image of the surface 104 or 108, as explained in more detail below.

Figure 2:
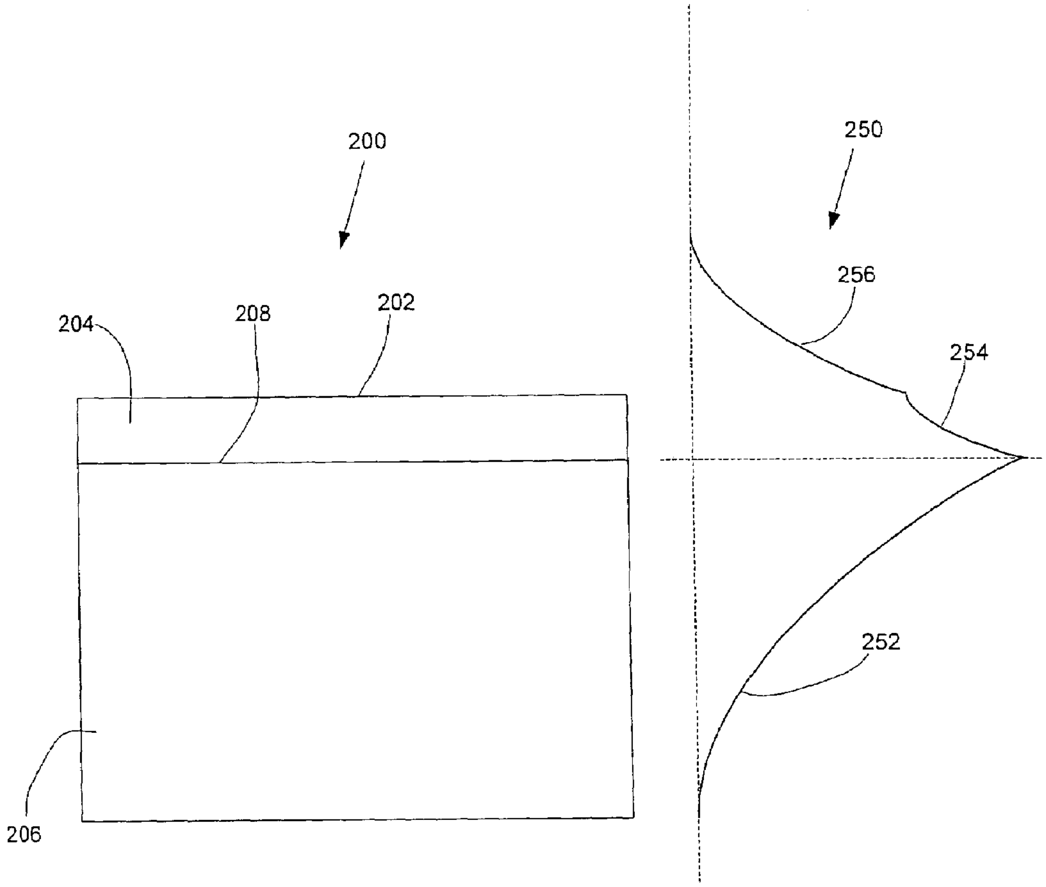
FIG. 2 is schematic side view of an object having a surface upon which a surface plasmon resonance can be excited, along with a schematic representation of the amplitude of the evanescent fields of the surface plasmon resonance.

FIG. 2 is schematic side view of an object 200 having a surface 202 upon which a surface plasmon resonance can be excited, along with a schematic representation 250 of the amplitude of the evanescent fields of the surface plasmon resonance. The object 200 has two materials 204 and 206 with dielectric constants having real parts with different signs, and the plasmon resonance is created at the interface 208 between the two materials. For example, one material 206 can be a polymer, and the other material 204 can be a thin conductive layer. One material can also include a photonic crystal (e.g., a vertical stack of alternating layers of material having different indices of refraction that). At the interface 208 between the two materials the amplitude of the plasmon field is greatest, and the field decays approximately exponentially as the field penetrates into the material.

Although the layer 204 is described as a conductive layer in the exemplary implementation of FIG. 1, it is not necessary for the layer 204 to be conductive for plasmons to be excited at the interface 208 between layers 204 and 206. Plasmons may occur in other configurations. For example, if the real parts of the dielectric constants of layers 204 and 206 have opposite signs at the interface 208, plasmons can be produced and one skilled in the art may find a number of configurations and material configurations that establish these conditions.

In one embodiment, the layer 204 may include vanadium dioxide, which is known to undergo an insulator-to-metal or semiconductor-to-metal phase transition at a certain temperature, as described in R. Lopez, L. A. Boatner, T. E. Haynes, L. C. Feldman, and R. F. Haglund, Jr., "Synthesis and characterization of size-controlled vanadium dioxide nanocrystals in a fused silica matrix," Journal of Applied Physics, Volume 92, Number 7, Oct. 1, 2002, which is incorporated herein by reference. By incorporating vanadium dioxide into the structure, the ability to produce plasmons could be switched on or off depending on the temperature of the material.

If a layer 204 is thinner than the penetration depth of the plasmon field (e.g., the depth in the material at which the amplitude of the plasmon field is reduced by 1/e) then an appreciable amplitude of the plasmon field can leak out of the layer 204. For example, when a surface plasmon resonance is excited by coherent radiation having a wavelength of about 1 μm, the 1/e depth of the evanescent plasmon field in a gold layer is on the order of a few hundred nm. The penetration depth of the field in a material is determined by the imaginary part of the material's dielectric constant, which, in turn, depends on the electromagnetic properties of the material and the wavelength of the radiation. The penetration depth generally is greater for longer wavelength excitation radiation. Thus, the amplitude of the plasmon field in the dielectric layer 206 can be represented by a decaying exponential curve 252, while the amplitude of the plasmon field in layer 204 can be represented by the decaying exponential curve 254. Outside of the layer 204, the amplitude of the plasmon field can be represented by a third decaying exponential curve 256.

Figure 3:
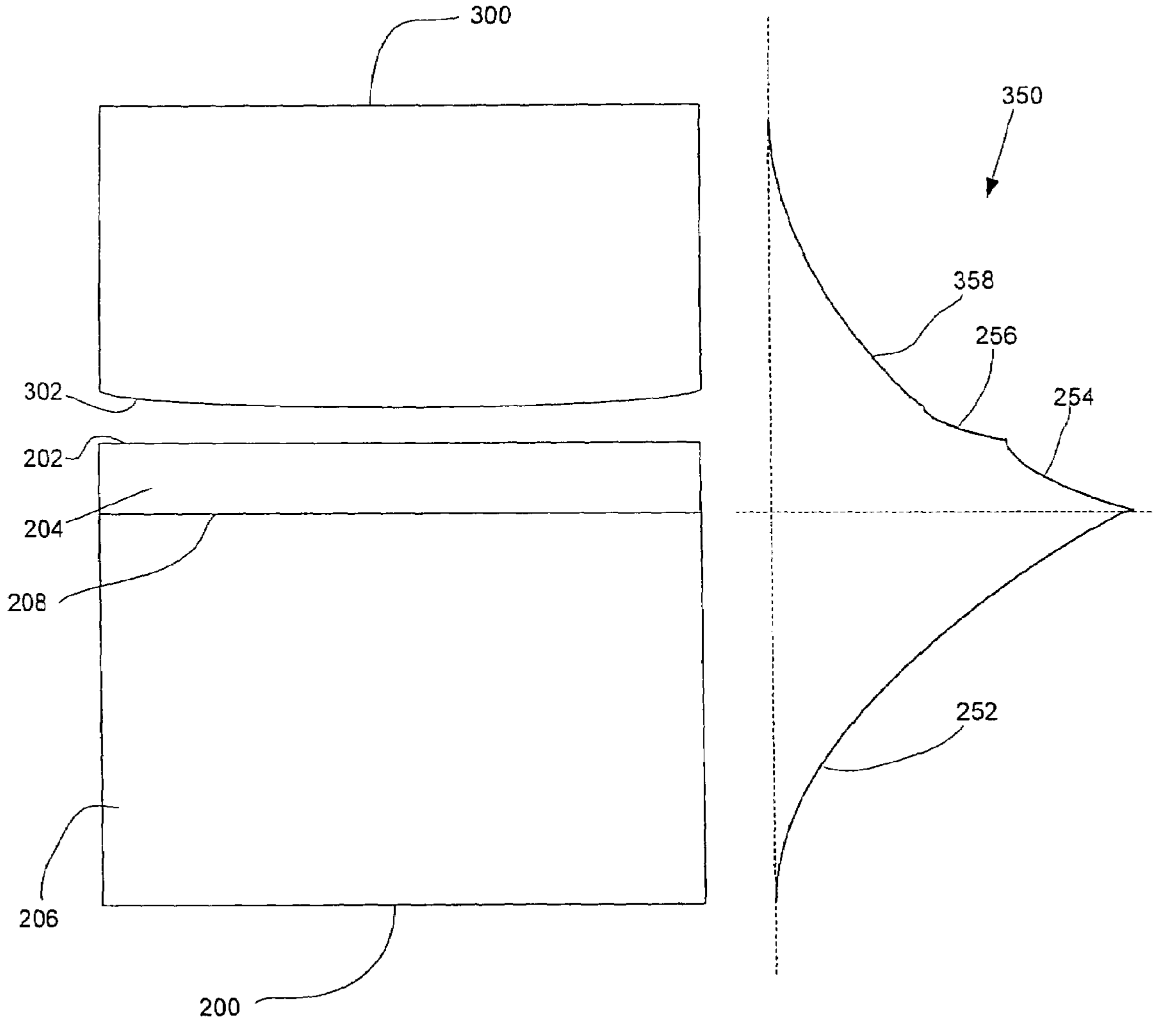
FIG. 3 is schematic side view of an object having a surface upon which a surface plasmon resonance can be excited in close proximity to the surface of another object, along with a schematic representation of the amplitude of the evanescent fields of the surface plasmon resonance.

FIG. 3 is schematic side view of an object 200 having a surface upon which a surface 202 plasmon resonance can be excited in close proximity to the surface 302 of another object 300, along with a schematic representation 350 of the amplitude of the evanescent fields of the surface plasmon resonance. As shown in FIG. 3, the evanescent field of the surface plasmon resonance includes a portion 256 that extends outside of the layer 204 into the gap between the surfaces 302 and 202 of the objects and a portion 358 that extends into the object 300. Because the imaginary part of the dielectric constant of the materials determines the penetration depth of the surface plasmon field and also the dissipation of energy in the plasmon resonance as the resonance travels parallel to the interface 208, the presence of different materials close to the interface can affect the degree to which plasmon energy is attenuated as the resonance travels parallel to the interface. By measuring plasmon energy attenuation as plasmons travel parallel to the interface along different paths, relative distances between surfaces 202 and 302 can be determined, and a profile of surface 302 and/or 202 can be generated.

Referring again to FIG. 1, plasmons can be excited at multiple positions 132 on the surface 108, and then the energy of the plasmons can be detected at a detection location on the surface. Plasmon energy can also be detected at multiple different detection positions 134 on the surface when the detected plasmon energy travels along different paths from one or more excitation positions 132 to the detection positions 134. Data corresponding to the energy received at the detection position 132 and the path traveled by the plasmon from the excitation positions 132 to the detection positions 134 when the plasmons travel along different paths can be stored in the memory 142. The data then can be deconvolved by the processor 142 to determine generate an image of surface 108 or 104. Although many deconvolution techniques and processes are known, some are described in U.S. Pat. No. 4,063,549 and in U.S. Pat. No. 4,646,256.

In one implementation, when only object 106 is present, plasmon energy can be detected at multiple detection positions 134 after plasmon resonances having approximately the same initial energy are excited at multiple excitation positions 132. Data concerning an amount of plasmon energy detected at the detection positions 134 and the path traveled by the plasmon from the excitation positions to the detection positions are used to determine an amount of attenuation along each path. Then, because different thicknesses of the surface layer 122 attenuate the plasmon energy by different amounts, information about the amount of attenuation along each path can be deconvolved to create an image of the relative thickness in the z-direction of the surface layer 122 as a function of position on the surface 108 in the x- and y-directions. If the absolute thickness of the surface layer 122 is known at any one position, then this information can be combined with knowledge of the relative thicknesses at different positions on the surface 108 to determine the absolute thicknesses of the surface layer 122 at different positions in the x- and y-directions on the surface 108.

In another implementation, when the surface 104 of object 102 is in close proximity to the surface 108 of object 106, measurements of plasmon energy attenuation can be used to determine a profile of the surface 106. The thickness of the surface layer 122 can be assumed to be uniform, and the surface 108 can be assumed to be flat. When surface plasmons are excited at excitation positions 132 and travel to detection positions 134, the degree to which the plasmon energy is attenuated as the plasmon travels along a path from the excitation position to the detection position will depend on the distance between surfaces 108 and 104, and, therefore, how far the evanescent plasmon field penetrates into the object 102 as the plasmon travels along the path. Thus, data concerning an amount of plasmon energy detected at detection positions 134 and the paths traveled by the plasmon from excitation positions 132 to detection positions 134 can be used to determine an amount of attenuation along each path, which information can be deconvolved to determine a relative distances in the z-direction between surfaces 104 and 108 as a function of position on the surface 108 in the x- and y-directions, i.e., z(x, y). An absolute distance between surfaces 104 and 108 can be determined, for example, from the height of a positioning structure 110 located between surfaces 104 and 108.

In another implementation, baseline measurements can be made on the surface 108 before surface 104 is brought into close proximity with surface 108 and the surface 104 is profiled. For example, without the presence of object 102, surface plasmons can be excited and detected on the surface 108, and information about the amount of attenuation along each path can be deconvolved to create an image of the relative thickness of the surface layer 122 as a function of x-y position on the surface 108. These data can be stored as calibration data in memory 142 and used to calibrate measurements used to profile the surface 104, when surface is in close proximity to surface 108. For example, after obtaining the calibration data and bringing surface 108 into close proximity with surface 104, surface plasmons can be excited and detected on the surface 108 and information about the amount of attenuation along paths that are similar to paths used to obtain the calibration data can be compared with the calibration data. For example, if the amount of attenuation along a particular path changes substantially when the surface 108 is brought close to surface 104, then the surfaces are quite close together along that path. However if the amount of attenuation along a different path changes very little when the surface 108 is brought close to surface 104, then the surfaces are relatively far apart along that different path. Moreover, the calibration data can be used to remove effects caused by a non-uniform thickness of layer, when generating a profile of surface 104 from the information about the attenuation of plasmon energy along multiple paths on surface 108 when surface 104 is in close proximity to surface 108.

Figure 4:
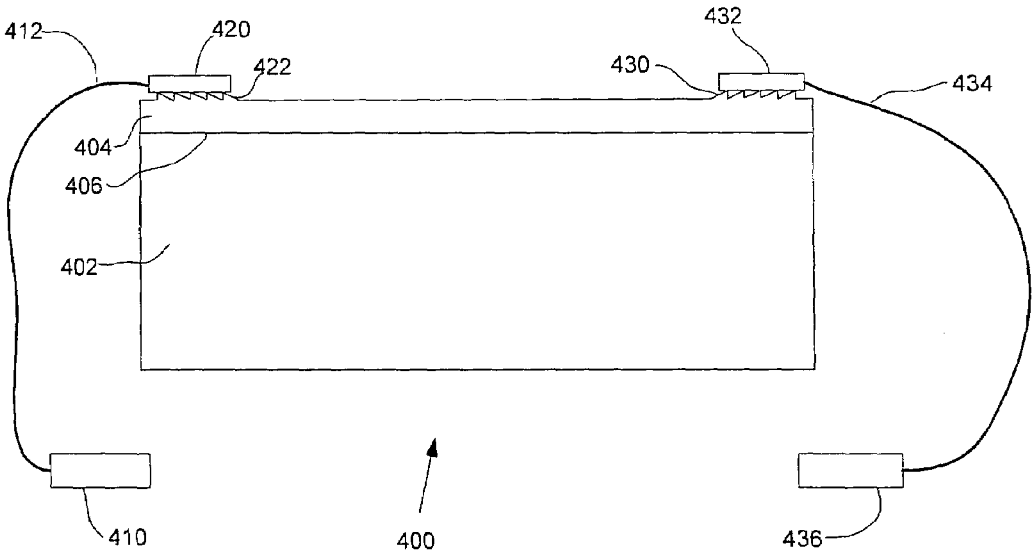
FIG. 4 is a schematic side view of a system for exciting a surface plasmon resonance at a first position on the surface of an object and for detecting energy in the surface plasmon resonance at another position on the surface.

FIG. 4 is a schematic side view of a system for exciting a surface plasmon resonance at a first position on the surface of an object and for detecting energy in the surface plasmon resonance at another position on the surface. The object 400 has a layer of material 402 and another layer of material 404, and the materials have dielectric constants with real parts having opposite signs. Thus, a plasmon resonance can be excited at the interface 406 between the two layers of material. To couple energy to the surface plasmon resonance, optical energy can be shined through one of the layer onto the interface, as shown in FIG. 1.

In another implementation, a laser 410 can generate optical energy that is directed toward the upper layer 404, either in a direct path from the laser or through a waveguide 412 (e.g., an optical fiber). The optical energy can be coupled into the object 400 and to the interface 406 through a coupler 420 on the surface of the object. For example, the coupler 420 can direct light toward a Bragg grating 422 that scatters the optical energy into the layer 404 to the interface 406 where a plasmon resonance is excited.

Plasmon energy can be coupled out of the object in a similar manner. For example, plasmon energy can be scattered by a Bragg grating 432 and converted into optical energy that is picked up by a coupler 430 that directs the optical energy into a waveguide 434 (e.g., an optical fiber). The waveguide 434 can transport the optical energy to a detector 436 that measures that amount of optical energy.

Other methods of coupling energy between electromagnetic waves and plasmons are possible, some of which are described in W. L. Barnes, A. Dereux, and T. W. Ebbesen, "Surface plasmon subwavelength optics," Nature, Volume 424, Aug. 14, 2003, 824-830, which is incorporated herein by reference. These methods include and are not limited to coupling through a prism, coupling by scattering from a topological defect on the surface on which the plasmon is to be generated, and coupling through a periodic corrugation in the surface on which the plasmon is to be generated.

Figure 5A:
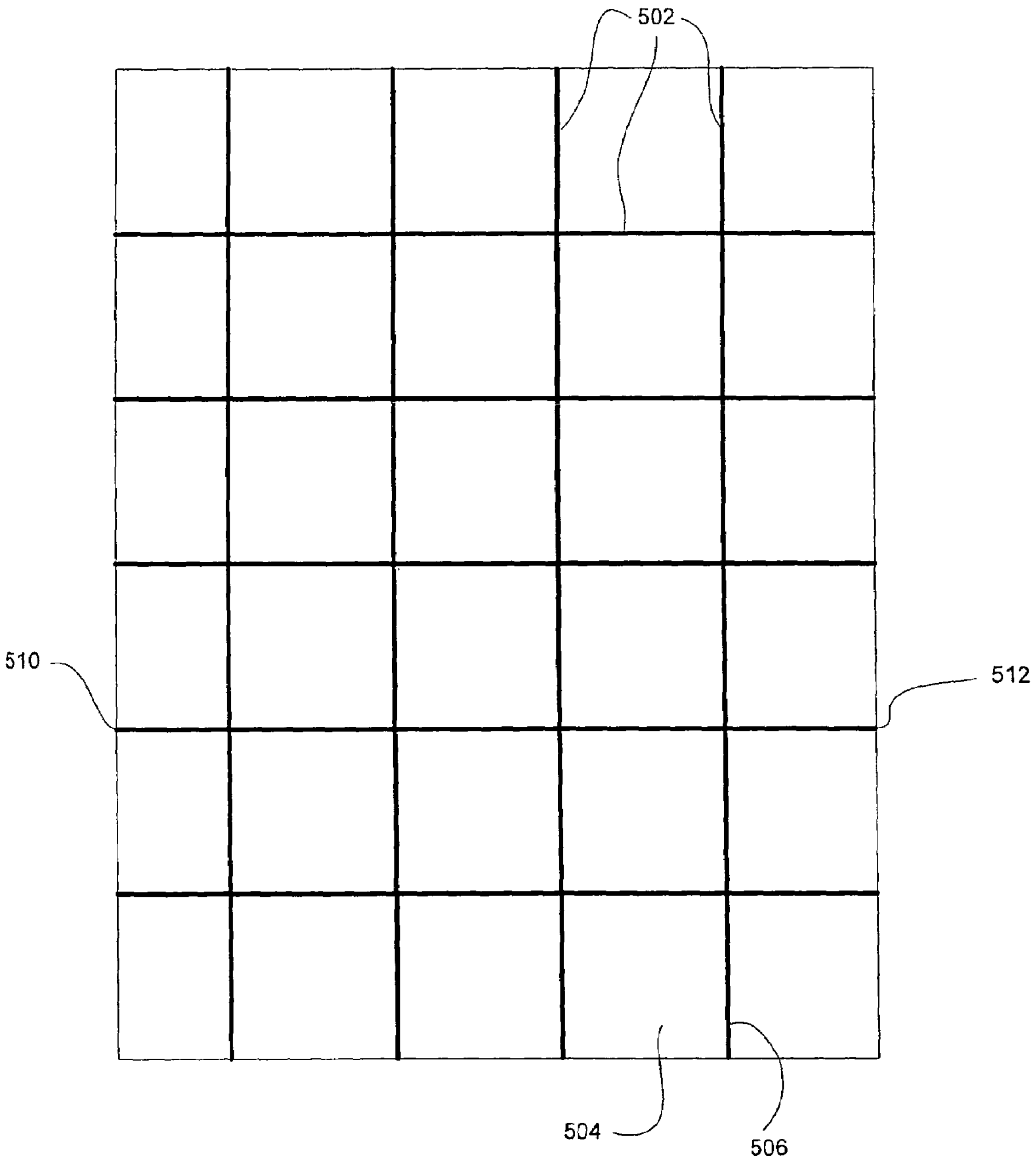
FIG. 5A is a schematic top view of a surface having several guides for guiding a surface plasmon resonance.
Figure 5B:
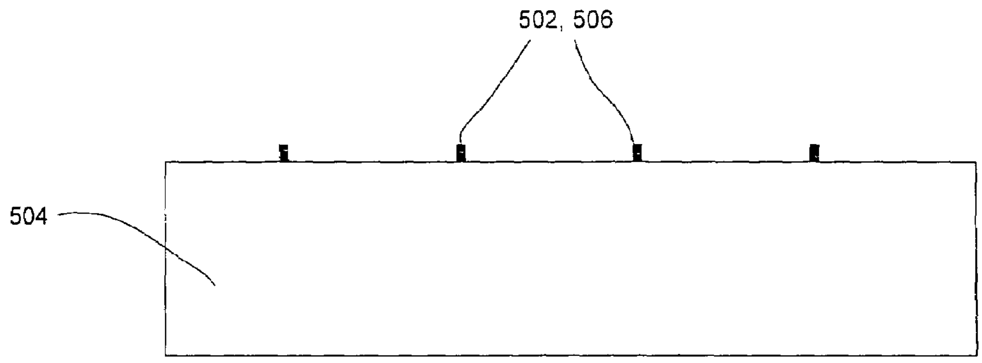
FIG. 5B is a schematic side view of a surface having several guides for guiding a surface plasmon resonance.

FIGS. 5A and 5B are schematic top and side views, respectively, of a surface having several guides for guiding a surface plasmon resonance. The guides 502 can be formed by a first material 504 that overlays a second material 506, where the first and second materials have dielectric constants with opposite signs to their real parts. For example, the second material 506 may be a semiconductor, and the first material 504 may be a metallization layer deposited on the second material. When a plasmon resonance is excited at the interface of the first and second materials, the plasmon can travel parallel to the interface and can be guided along the path of a guide 502. Thus, the guides 502 provide a predictable path for the plasmons to travel from an excitation position to a detection position.

In one implementation, the guides 502 can cross the surface from one perimeter position of the surface to another perimeter position. A surface plasmon resonance can excited at a position 510 at one perimeter position, and the energy in the plasmon can be detected at another position 512 at another perimeter position on the surface.

The guides 502 can be located on a mask that is placed in close proximity to a semiconductor wafer, so that a pattern in the mask can be transferred into the wafer. In one implementation, the guides 502 can form part of the pattern in the mask. By collecting and deconvolving information about the attenuation of plasmon energy as plasmons travel along guides from an excitation position to a detection position, the distance between the mask and the semiconductor can be determined across the surface of the mask and the semiconductor wafer. If the distance does not conform to a desired distance at certain locations on the surface, the distance can be adjusted a one or more positions, and then the distance can be measured again.

Figure 6:
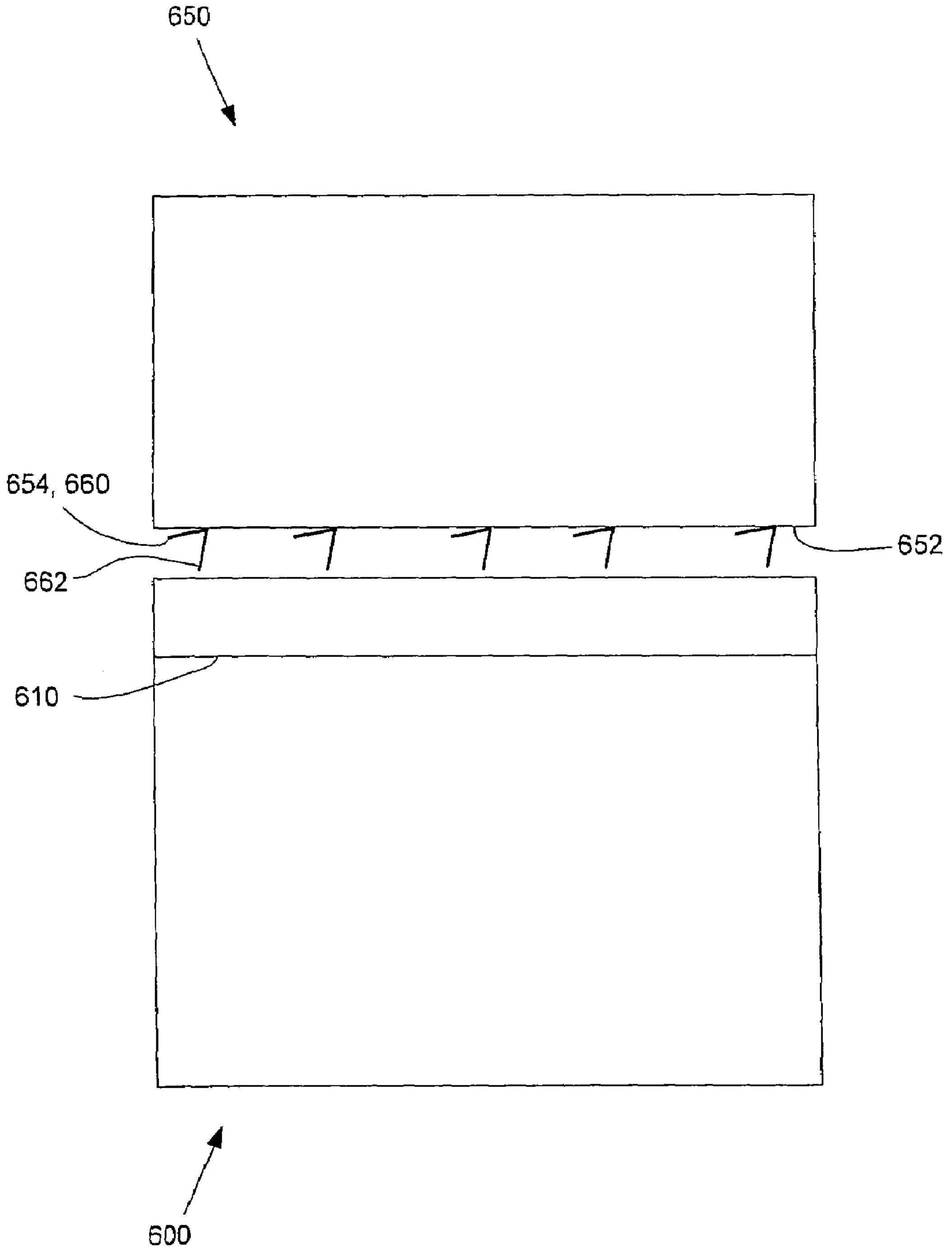
FIG. 6 is a schematic side view of an object having a surface upon which a surface plasmon resonance can be excited in close proximity to an object having a surface that can be altered.

FIG. 6 is a schematic side view of an object 600 having a surface upon which a surface plasmon resonance can be excited in close proximity to an object 650 having a surface that can be altered. In one implementation, the object 650 can have a surface 652 with one or more objects 654 that can be moved or altered. For example, the object can be a microelectromechanical structure (e.g., a mirror or a carbon nanotube) whose position can be moved when a signal is applied to the structure. For example, the structure can be moved from a first position 660 to a second position 662 when the signal is applied to the structure.

One or both of the objects 600 and 650 can include an interface 610 between two materials having dielectric constants with real parts having opposite signs, and a surface plasmon resonance can be excited at the interface. By collecting and deconvolving information about the attenuation of plasmon energy as plasmons travel along the interface 610 following multiple paths from excitation positions to detection positions, the distance between the facing surfaces of objects 600 and 650 can be determined at multiple points on the surfaces. Measurement of the distance between the surfaces can be used to determine whether the moveable objects 654 have moved and to image the surface 652 including the moveable objects before and after movement of the objects 654. In another implementation, the moveable objects 654 can be products of physical, chemical, and/or biological reactions, and movement of the object 654 can correspond to the occurrence of a reaction. For example, a biological protein may be assembled on the surface 652, and measurement of the distance between facing surfaces of the objects 600 and 650 can be used to determine whether the reaction has occurred, and to image the surface 652 including the reaction products before and after the reaction.

Figure 7:
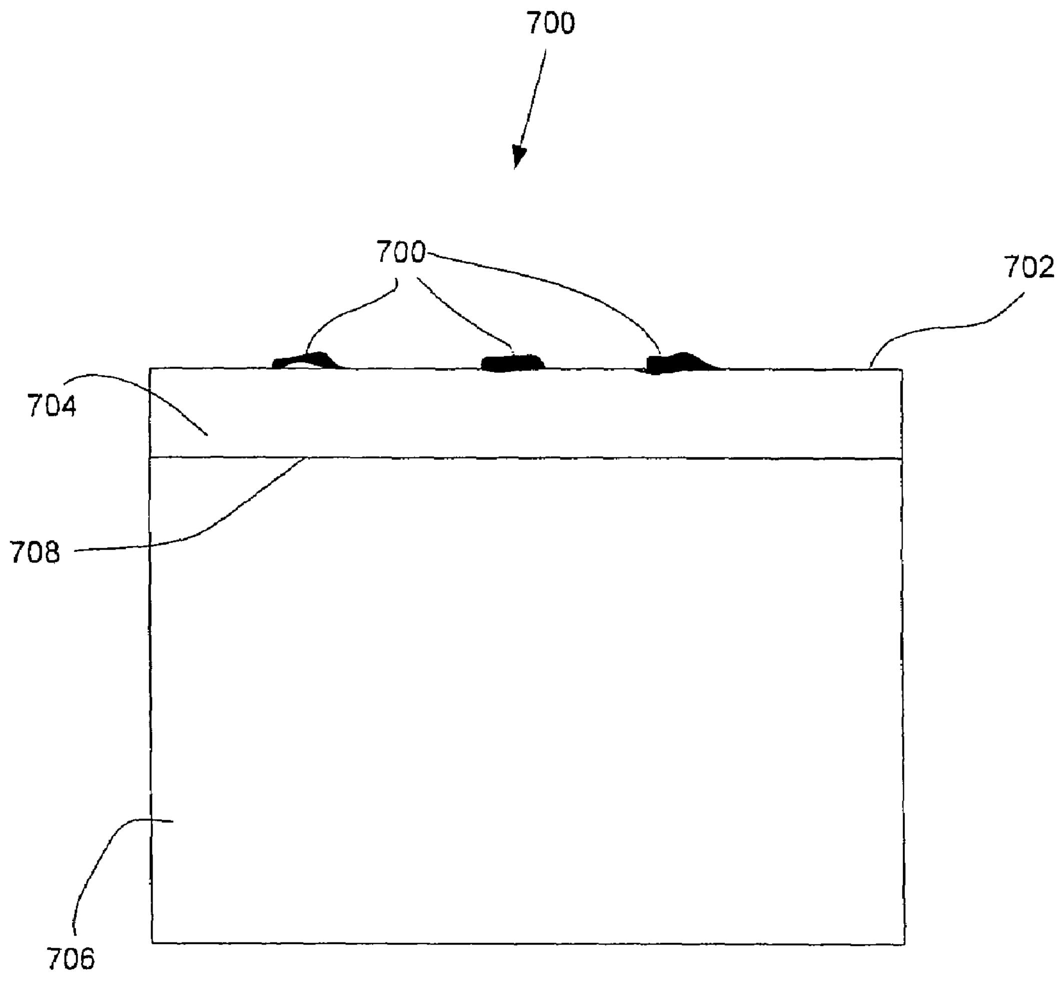
FIG. 7 is a schematic side view of an object having a surface that can be altered and upon which a surface plasmon resonance can be excited.

FIG. 7 is a schematic side view of an object 700 having a surface 702 that can be altered and upon which a surface plasmon resonance can be excited. The object 700 has two materials 704 and 706 with dielectric constants having real parts with different signs, and the plasmon resonance is created at the interface 708 between the two materials. For example, one material 706 can be a polymer, and the other material 704 can be a thin conductive layer. At the interface 708 between the two materials the amplitude of the plasmon field is greatest, and the field decays approximately exponentially as the field penetrates into the material. Plasmons can be excited at excitation positions on the surface 702 of the object and detected at detection positions, and by recording measurements of the attenuation of plasmon energy as the plasmons travel over multiple paths from excitation positions to detection positions, baseline measurements on the object can be made and recorded. Then, after the baseline measurements have been recorded, the surface 702 can be altered. For example, material 710 can be deposited on the surface 702, or a chemical or biological reaction can occur at the surface, which results in material 710 adhering to surface 702 or in an alteration of the surface. After alteration of the surface, plasmons again can be excited at excitation positions on the surface 702 and detected at detection positions. By measuring the attenuation of plasmon energy as the plasmons travel over multiple paths on the altered surface and comparing the measurements with the recorded baseline measurements, a profile of the altered surface as it compares with the original surface can be generated.

Figure 8:
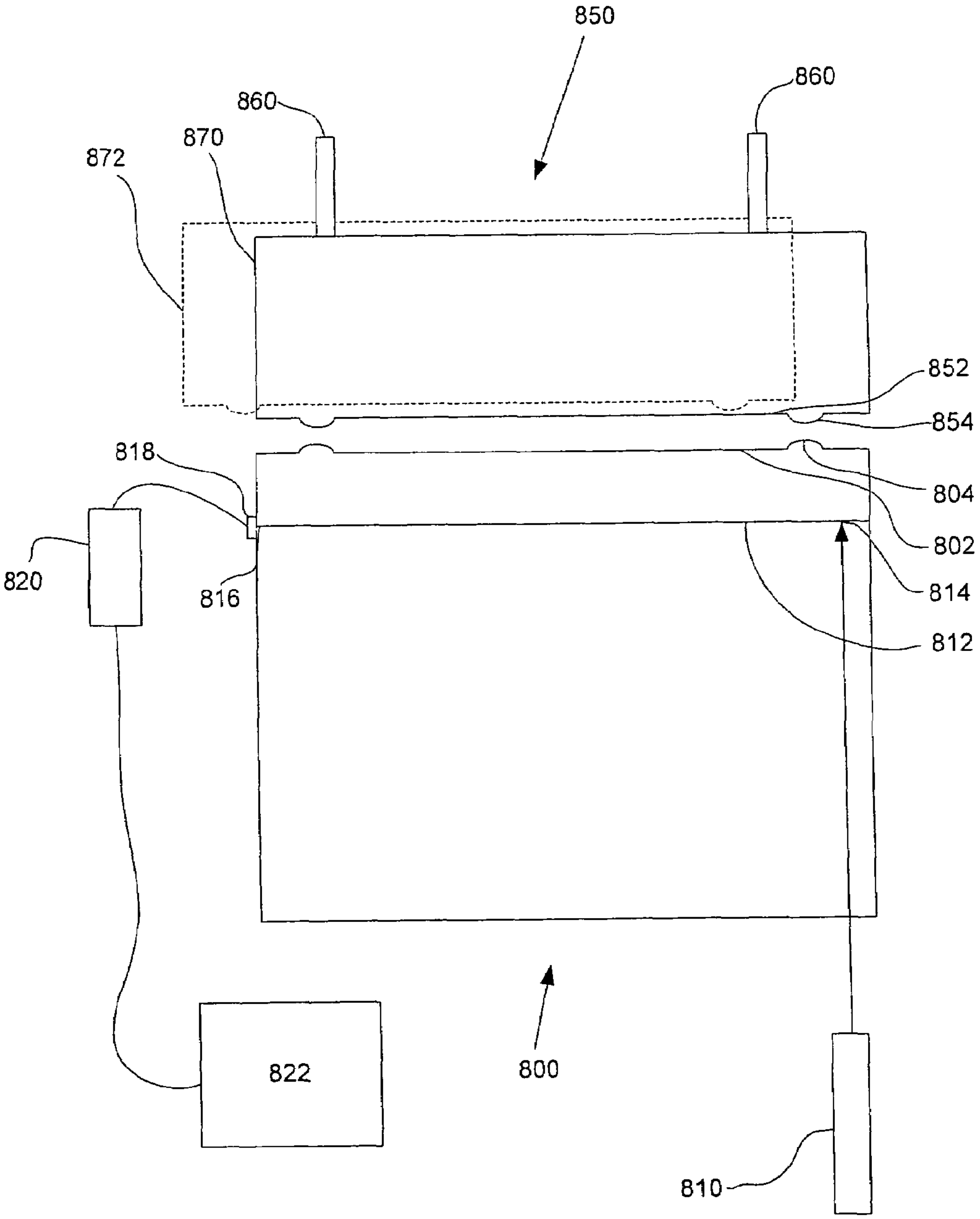
FIG. 8 is a schematic side view of an object having a surface upon which a surface plasmon resonance can be excited and having alignment guides in close proximity to an object having a surface with complementary alignment guides.

FIG. 8 is a schematic side view of an object 800 having a surface 802 upon which a surface plasmon resonance can be excited and having alignment guides 804 in close proximity to another object 850 having a surface 852 with complementary alignment guides 854. An optical energy source 810 can provide optical energy to an interface 812 between two different materials within object 800 to excite a plasmon resonance at an excitation position in the object 800. The plasmon energy can be transported along the interface to a detection position 816, where a coupler 818 couples the plasmon energy into optical energy that is guided to a detector 820. The detector 802 produces a signal proportion to the plasmon energy at the detection position, and information in the signal is processed by a processor 822.

Object 850 can be moved relative to object 800 by positioning structures 860. When the object is moved into a position 870 in which its alignment guides 804 are aligned with the alignment guides 854 of the object 850, such that a separation between alignment guides 804 and 854 is minimized, the attenuation of plasmon energy as the plasmon travels from the excitation position 814 to the detection position 816 is either minimized or maximized. When the object 850 is moved into a position 872 in which the guides 804 and 854 are not aligned, the attenuation of plasmon energy will not take on an extreme value. Thus, objects 800 and 850 can be aligned by continuously or repeatedly exciting a plasmon at an excitation position 814 while detecting the plasmon energy at a detection position 816 and monitoring the detected amount of plasmon energy. When the amount of plasmon energy detected reaches an extremum (i.e., either a maximum or a minimum), the objects are aligned.

Figure 9A:
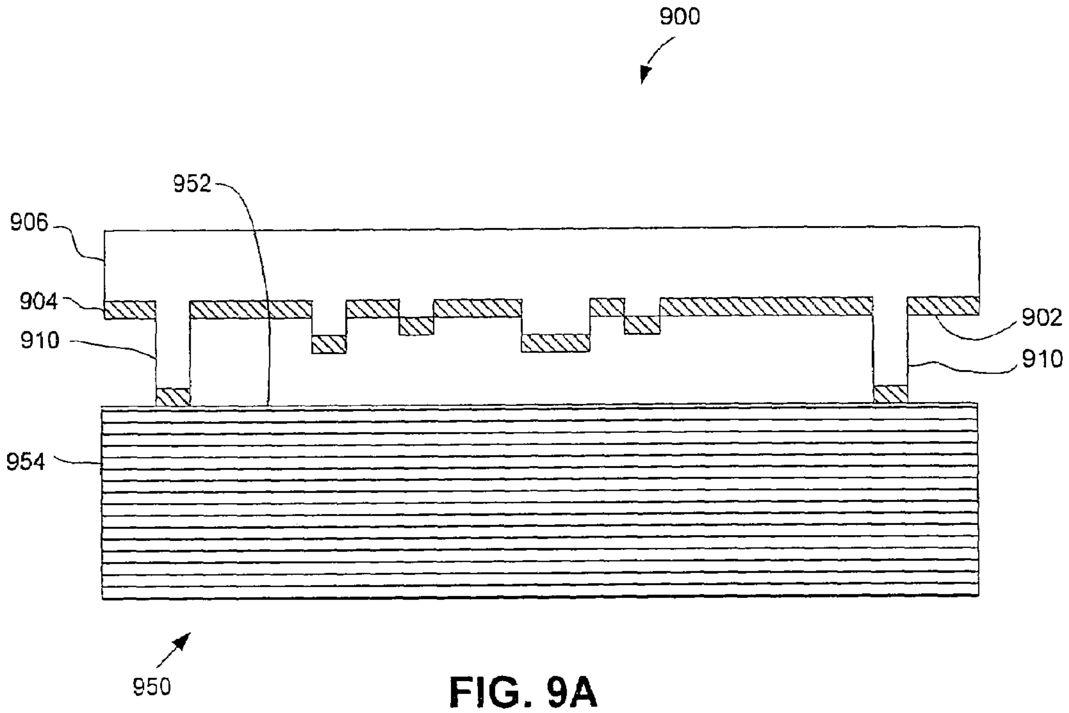
FIG. 9A is a schematic side view of a mask in close proximity to an alterable object.
Figure 9B:
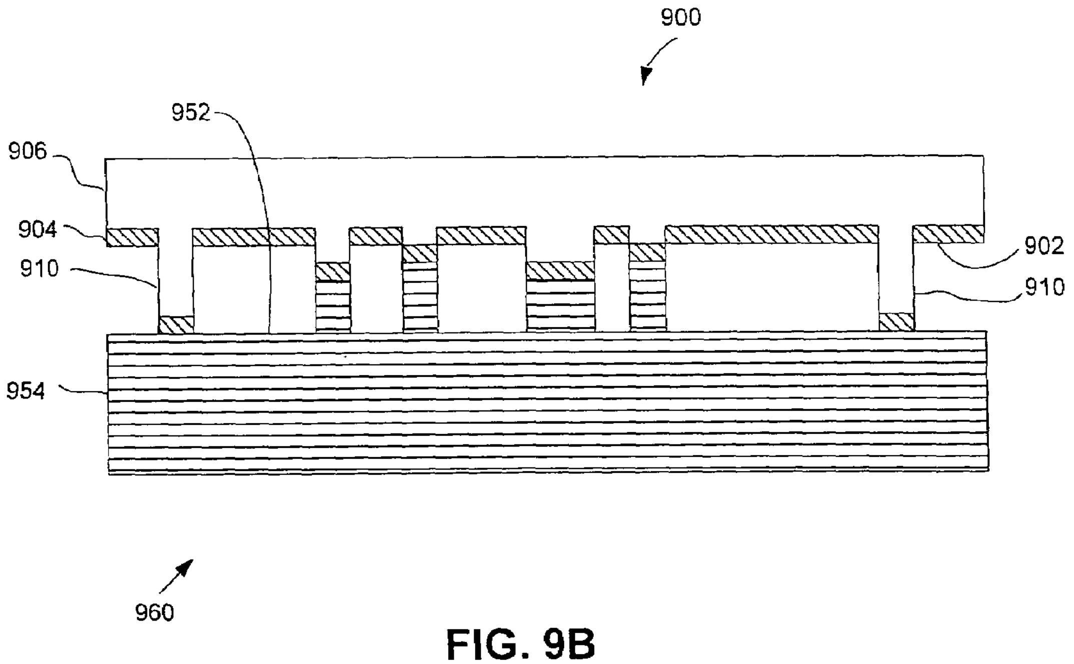
FIG. 9B is a schematic side view of a mask in close proximity to an alterable object after the object has been altered.

FIGS. 9A and 9B are schematic side views of a mask 900 in close proximity to an alterable object 950 that can be deformed into a new shape 960. The mask has a surface 902 that includes a profile that can be transferred to the alterable object. Material 904 at the surface 902 has a dielectric constant with a real part that is either positive or negative. A layer of material 906 under the surface material 904 has a dielectric constant with a real part that has a sign that is opposite to the sign of the surface layer's dielectric constant. For example, layer 906 can be a transparent insulator or a semiconductor layer, and layer 904 can be a metallization layer. Thus, a plasmon can be excited at the interface between layers 904 and 906.

The surface 902 of mask 900 is in close proximity to the surface 952 of the alterable object 950. For example, positioning structures 960 can maintain a gap between the surfaces 902 and 952, as shown in FIG. 9A. By exciting plasmon resonances at excitation positions on the surface 952 and detecting plasmon energy at detection positions on the surface, measurements of plasmon energy attenuation can be made as the plasmons traverse different paths on the surface. Information about the plasmon energy attenuation over the different paths can be deconvolved to generate an image of the profile of the mask surface 952 and of the distance between the mask and the surface 902. This information can be stored as baseline information.

As shown in FIG. 9B, the object 960 can include a material 954 (e.g., a polymer material) that can be deformed. For example, the material 954 can be heated above a polymer-glass transition temperature, such that the material flows and takes on a complementary shape to the profile of the mask surface 902. After deforming the object 960 plasmon resonances again can be excited at excitation positions on the surface 952 and the plasmon energy can be detected at detection positions on the surface. Measurements of plasmon energy attenuation can be made as the plasmons traverse different paths on the surface. Information about the plasmon energy attenuation over the different paths can be deconvolved and compared to the baseline information recorded before the object 950 was deformed to generate an image of the surface 962 of the deformed object 960. The material 954 can then be cooled, and the deformed object 960 can be separated from the mask 900.

Figure 10:
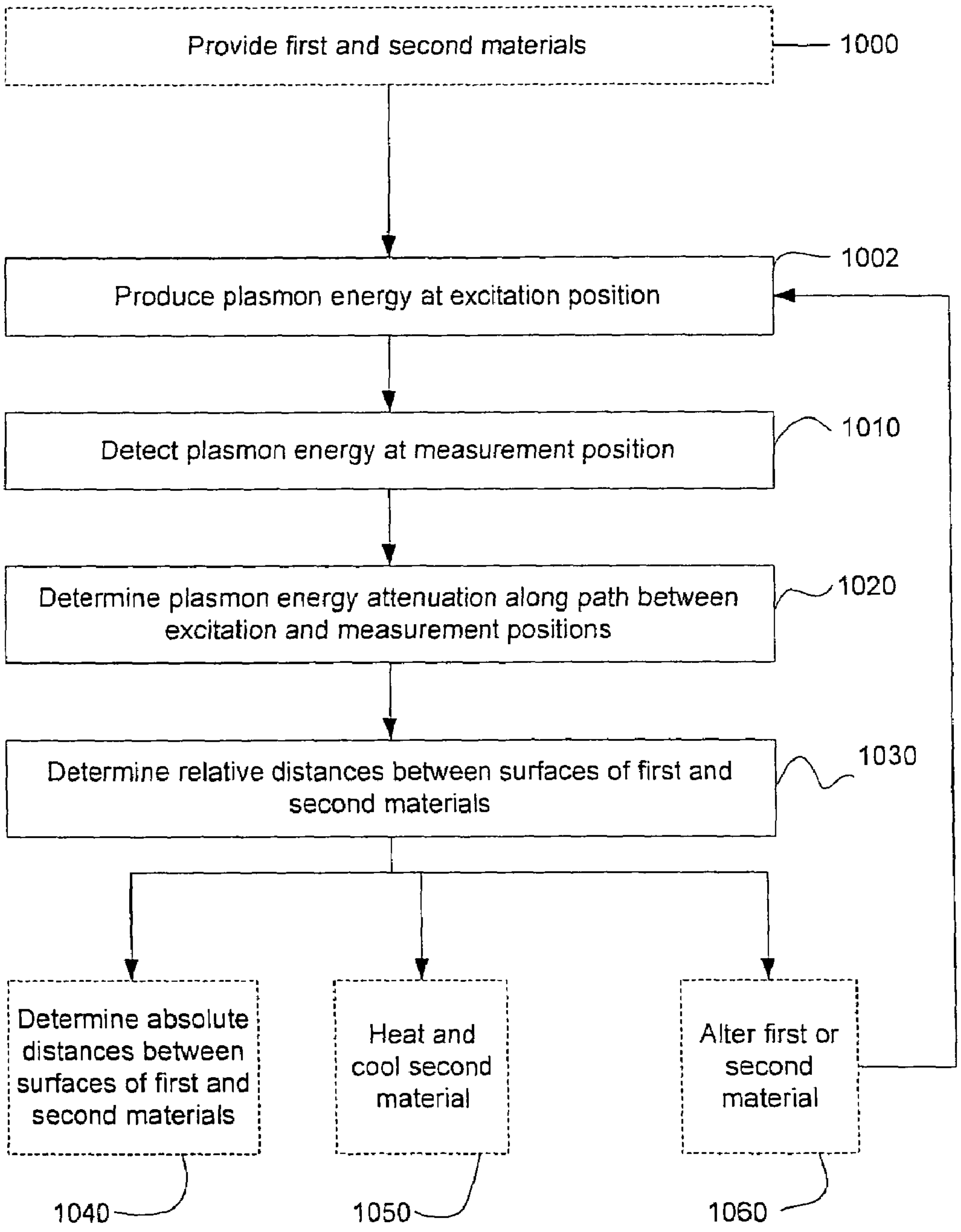
FIG. 10 is a flow diagram illustrating a method of determining relative distances between two surfaces in accordance with some of the embodiments.

FIG. 10 is a flow diagram illustrating a method of determining relative distances between two surfaces in accordance with some of the embodiments. The method generally begins at block 1002, whereupon plasmon energy is produced by exciting a plasmon resonance at least one excitation position on a first surface of a first material. The plasmon energy can be produced by providing optical energy to the first surface (e.g., by illuminating at least a portion of the first surface with laser light or by providing a coherent beam of electromagnetic radiation to the first surface). The first material can include a conductive layer and/or a photonic crystal.

At block 1010 the plasmon energy is detected at least one measurement position on the first surface after the plasmon energy has propagated from the at least one excitation position to the at least one measurement position. The excitation positions and/or measurement positions can be located along a periphery of the first surface.

At block 1020 an attenuation of plasmon energy is determined along a plurality of paths between the at least one excitation position and the at least one measurement position. The first or second surface can define a portion of a mask, and the other of the first or second surfaces can define a portion of a substrate. The mask can include a plurality of plasmon guides on the first surface and the plasmon guides can define a plurality of paths on the first surface. The plurality of plasmon guides can be disposed substantially parallel to one another on the first surface.

At block 1030 relative distances are determined between the first surface and a second surface of a second material at a plurality of points on at least one of the surfaces based on the determined attenuation of plasmon energy along the plurality of paths.

At optional block 1040 absolute distances between the first surface and the second surface at the plurality of points can be determined based on the relative distances and on a known distance between the first surface and the second surface at one of the points.

At optional block 1000 the first material having the first surface can be provided and the second material can be provided having the second surface facing the first surface.

At optional block 1050, when the first surface is a patterned surface and the second material includes a polymer, the second material can be heated above a polymer-glass transition temperature until a pattern corresponding to the patterned surface of the first surface is created in the second material and then the second material can be cooled below the polymer-glass transition temperature.

At optional block 1060 the first or second surface can be altered after determining relative distances between the first surface and the second surface. For example, a micro-electro-mechanical structure can be moved on the altered surface, a structure can be moved across the altered surface, or a reaction can be catalyzed between materials of the first or second surface and another material.

In this disclosure, references to "optical" elements, components, processes, or other aspects, as well as references to "light" may also relate in this disclosure to so-called "near-visible" light such as that in the near infrared, infra-red, far infrared and the near and far ultra-violet spectrums. Moreover, many principles herein may be extended to many spectra of electromagnetic radiation where the processing, components, or other factors do not preclude operation at such frequencies, including frequencies that may be outside ranges typically considered to be optical frequencies.

This detailed description sets forth various implementations of the devices and/or processes via the use of block diagrams, diagrammatic representations, and examples. Insofar as such block diagrams, diagrammatic representations, and examples contain one or more functions and/or operations, it will be understood as notorious by those within the art that each function and/or operation within such block diagrams, diagrammatic representations, or examples can be implemented, individually and/or collectively, by a wide range of hardware, materials, components, or virtually any combination thereof.

Those having skill in the art will recognize that a typical optical system generally includes one or more of a system housing or support, and may include electrical components, alignment features, one or more interaction devices, such as a touch pad or screen, control systems including feedback loops and control motors (e.g., feedback for sensing positions of optical elements (e.g., lens, filters, beam splitters, and detectors); control motors for moving/distorting optical elements to provide desired optical behavior). Such systems may include image processing systems, image capture systems, photolithographic systems, scanning systems, or other systems employing optical, RF, IR, UV, X-ray or other focusing or refracting elements or processes.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and electrical circuitry forming a communications device (e.g., a modem, communications switch, or optical-electrical equipment).

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or electrically interactable and/or electrically interacting components.

In one or more various aspects, related systems include but are not limited to circuitry and/or programming and/or electro-mechanical components for effecting the herein-referenced method aspects; the circuitry and/or programming and/or electro-mechanical components can be virtually any combination of hardware, software, firmware, and/or electro-mechanical components configured to effect the herein-referenced method aspects depending upon the design choices of the system designer in light of the teachings herein. Some portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter subject matter described herein are capable of being distributed as a machine-readable program product in a variety of forms, and that an illustrative embodiment of the subject matter subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

While particular embodiments of the present invention have been shown and described, it will be understood by those skilled in the art that, based upon the teachings herein, changes and modifications may be made without departing from this invention and its broader aspects and, therefore, the appended claims encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," "comprise" and variations thereof, such as, "comprises" and "comprising" are to be construed in an open, inclusive sense, that is as "including, but not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g.,"a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

All of the U.S. patents, U.S. patent application publications, U.S. patent applications, foreign patents, foreign patent applications and non-patent publications referred to in this specification and/or listed in any Application Data Sheet, are incorporated herein by reference, in their entireties.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:

producing plasmon energy by exciting a plasmon resonance at least one excitation position on a first surface of a first material facing a second surface of a second material, wherein the plasmon energy propagates to a measurement position along the first surface;

detecting an amount of plasmon energy at the measurement position on the first surface after the plasmon energy has propagated from the excitation position to the measurement position; and adjusting a relative position between the first and second surfaces based on the amount of plasmon energy detected at the measurement position.

2. The method of claim 1, wherein the second material comprises a semiconductor material.

3. The method of claim 1, wherein the first material comprises a patterned mask.

4. The method of claim 1, further comprising:

providing the first material having the first surface; and providing the second material having the second surface facing the first surface.

5. The method of claim 1, further comprising producing plasmon energy by exciting a plasmon resonance at the at least one excitation position on the first surface, detecting an amount of plasmon energy at the measurement position on the first surface after the plasmon energy has propagated from the excitation position to the measurement position, and adjusting a relative position between the first and second surfaces based on the amount of plasmon energy detected at the measurement position until the amount of plasmon energy detected at the measurement position is substantially equal to a desired amount of plasmon energy.

6. The method of claim 1, wherein the first surface includes a first deformity and wherein the second surface includes a second deformity.

7. The method of claim 6, wherein the first deformity and the second deformity are protrusions from the surfaces.

8. The method of claim 1, wherein the first surface includes a first deformity and wherein the second surface includes a second deformity and wherein the first deformity and the second deformity are aligned along a direction substantially perpendicular to the first and second surfaces when the detected amount of plasmon energy is substantially equal to a desired amount of plasmon energy.

9. An apparatus comprising:

positioning structures configured to align a first surface of a first material with a second surface of a second material;

an optical energy source, wherein the source is alignable to provide electromagnetic radiation at a frequency operative to excite a plasmon resonance at least one excitation position on the first surface of the first material wherein plasmon energy propagates to at least one measurement position along the first surface that is spatially separated from the at least one excitation position; and a detector configured to produce a signal corresponding to propagated plasmon energy measured at the at least one measurement position on the first surface spatially separated from the at least one excitation position;

wherein the positioning structures are configured to adjust a relative position between the first and second surfaces in response to the signal.

10. The apparatus of claim 9, wherein the positioning structures comprise:

a movable stage configured to align the first surface with the second surface; and the apparatus can further include a processor configured to process the signal corresponding to excited plasmon energy to provide a signal to the movable stage to move the first or second surfaces into an alignment position with the other of the first or second surface.

11. The apparatus of claim 9, wherein the second material comprises a semiconductor material.

12. The apparatus of claim 9, wherein the first material comprises a patterned mask.

13. The apparatus of claim 9, wherein the first surface includes a first deformity and wherein the second surface includes a second deformity.

14. The apparatus of claim 13, wherein the first deformity and the second deformity are protrusions from the surfaces.

15. The apparatus of claim 13, wherein the detector is configured to produce a signal corresponding to an amount of excited plasmon energy at the at least one measurement position on the first surface, wherein the positioning structures are configured to align the first deformity and the second deformity along a direction substantially perpendicular to the first and second surfaces when the detected amount of plasmon energy is substantially equal to a desired amount of plasmon energy.

16. The apparatus of claim 9, wherein the detector comprises a coupler adapted for coupling plasmon energy at the at least one measurement position into an electromagnetic wave.

17. The apparatus of claim 16, wherein the coupler comprises a diffraction grating.

* * * * *

UNITED STATES PATENT AND TRADEMARK OFFICE

CERTIFICATE OF CORRECTION

PATENT NO. : 7,463,359 B2
APPLICATION NO. : 11/402305
DATED : December 9, 2008
INVENTOR(S) : Roderick A. Hyde It is certified that error appears in the above-identified patent and that said Letters Patent is hereby corrected as shown below:

Col. 17, line 45
This phrase should read as follows: "...excite a plasmon resonance at at least one..."

Signed and Sealed this

Seventeenth Day of March, 2009

JOHN DOLL
*Acting Director of the United States Patent and Trademark Office*